United States Patent [19]
Johansson

[11] Patent Number: 5,801,237
[45] Date of Patent: Sep. 1, 1998

[54] METHOD FOR THE PURIFICATION OF SHORT NUCLEIC ACIDS

[75] Inventor: Hans Johansson, Upsala, Sweden

[73] Assignee: Pharmacia Biotech AB, Upsala, Sweden

[21] Appl. No.: 860,860

[22] PCT Filed: Jan. 18, 1996

[86] PCT No.: PCT/SE96/00043

§ 371 Date: Sep. 15, 1997

§ 102(e) Date: Sep. 15, 1997

[87] PCT Pub. No.: WO96/22299

PCT Pub. Date: Jul. 25, 1996

[30] Foreign Application Priority Data

Jan. 20, 1995 [SE] Sweden .................................. 9500183

[51] Int. Cl.$^6$ .......................... C07H 21/00; C07H 19/00; C07H 21/02; C12Q 1/68
[52] U.S. Cl. .......................... 536/25.4; 435/6; 536/25.41; 536/25.3; 536/27.1; 536/27.11; 536/27.12
[58] Field of Search .................. 435/6; 536/27.1, 536/27.11, 27.12, 25.3, 25.4, 25.41

[56] References Cited

U.S. PATENT DOCUMENTS 4,997,927  3/1991  Blocker et al. ........................ 536/27

FOREIGN PATENT DOCUMENTS

| | | | |
|---|---|---|---|
| WO 93/08201A1 | 4/1993 | WIPO. | |
| WO 95/27718A2 | 10/1995 | WIPO. | |
| WO 96/01268A1 | 1/1996 | WIPO. | |

OTHER PUBLICATIONS

Yeung et al, "A general method of optimizing automated DNA synthesis to decrease chemical consumption to less than half", Anal. Biochem. 187:66–75, 1990.

Cubellis et al, "Use of fast protein liquid chromatography for the purification of synthetic oligonucleotides", J. Chromatography 329:406–414, 1985.

Gaur, "High performance liquid chromatography of synthetic oligonucleotides" J. Chromatography 549:207–215, 1991.

*Primary Examiner*—W. Gary Jones
*Assistant Examiner*—Jeffrey Fredman
*Attorney, Agent, or Firm*—Birch, Stewart, Kolasch & Birch, LLP

[57] ABSTRACT

Method for the purification of a synthetic oligonucleotide from failure sequences comprising contacting a sample containing the desired oligonucleotide in protected water-soluble form with a hydrophilic adsorbent exhibiting anion exchange groups under conditions permitting binding of said oligonucleotide to said adsorbent, whereafter the adsorbed oligonucleotide is deprotected and separated from failure sequences. The characteristic feature of the method is to use an anion exchange adsorbent that binds the protected oligonucleotide under conditions of high as well as low ionic strength.

5 Claims, No Drawings

METHOD FOR THE PURIFICATION OF SHORT NUCLEIC ACIDS

TECHNICAL FIELD

Purification of synthetic oligonucleotides from mixtures in which the desired oligonucleotide contain a hydrophobic protecting group.

The number of nucleotide residues in a synthetic oligonucleotide may in principle be any integer >1. According to the synthetic routes employed today, the number is often <200 and usually <100.

Synthetic oligonucleotides comprise DNAs, RNAs and analogues containing modified bases, modified sugars and modified phosphate groups. A certain modification may be repeated in one, more or all of the nucleotide residues. A typical modification is thiolation in the backbone, e.g. the phosphate group may have one or two of its oxygen atoms replaced with sulphur (phosphorothioate and phosphorodithioate oligomers, respectively). Another typical modification is alkylation in certain bases, e.g. methylation.

TECHNICAL BACKGROUND AND PRIOR ART

The use of oligonucleotides as drugs will dramatically increase the demand for large scale production of highly purified synthetic oligonucleotides. Today oligonucleotides are typically synthesized by reacting, step-wise and in a predetermined order, 5'-protected nucleotides, activated at their respective phosphate group, with the deprotected 5-position in a terminal nucleotide residue of a growing oligonucleotide chain attached to a solid support. The most popular protecting groups for the 5'-position have been strongly hydrophobic with preference for 4,4'-dimethoxyphenylmethyl (dimethoxytrityl=DMTr). An alternative is 9-phenylxanthen-9-yl (pixyl=Px). The resulting 5-terminal protected oligonucleotides have typically been purified by combining chromatography on strongly hydrophobic matrixes (reverse phase chromatography=RPC) with anion exchange chromatography (IEX). In common for all RPC based purification procedures applied so far have been the use of water-soluble organic solvents (such as acetonitrile) to elute the adsorbed oligonucleotide.

A typical procedure for purification of oligonucleotides would, at minimum, include the following steps:

1. Cleavage of the oligonucleotide from the solid support used during the synthesis. This is normally done by adding concentrated ammonia (25%) at an elevated temperature for several hours.
2. Removal of ammonia.
3. RPC for removal of failure sequences lacking the protecting group in the 5-position in terminal nucleotide residues.
4. Deprotection either while the desired full length oligonucleotide is still adsorbed onto the RPC resin or after elution from the resin. Deprotection is normally carried out by treatment with weak acids.
5. Elution of the oligonucleotides from the RPC column by applying an increasing concentration of organic solvent, e.g. acetonitrile.
6. Loading of the previously eluted oligonucleotide onto an anion exchange column and subsequent elution by applying an increasing concentration of an inorganic salt.
7. Concentrating and formulating the desired product.

For the synthesis and purification of oligonucleotides, including analogues thereof, see for instance Methods in Molecular Biology 20 (1993) (Ed. Agrawal S, Humana Press, Totowa, N.J., U.S.A.).

It has been suggested to run the RPC steps in a column in which particulate forms of a strongly hydrophobic matrix and an anion exchange matrix have been intimately mixed (U.S. Pat. No. 4,997,927). This approach demands the use of organic solvents such as acetonitrile and dichloromethane.

DRAWBACKS OF THE PRIOR ART METHODS

The earlier known methods have several drawbacks that make large scale processes difficult and expensive to design. The handling of large amounts of organic solvents demands explosive safe equipment and toxicity precautions. The production costs are further increased by the recovery and disposal of organic solvents and by extra costs related to labour and chromatography equipment for running multi-step processes.

OBJECTS OF THE INVENTION

The objects of the invention is to provide a simplified, safer and cheaper method for the purification of synthetic oligonucleotides.

THE INVENTION

These objects are achieved by applying a sample containing the desired protected oligonucleotide in water-soluble form onto a hydrophilic chromatography media (adsorbent) that is substituted with anion exchange groups and that binds the oligonucleotide under conditions of high as well as low ionic strength (for instance corresponding to a concentration of NaCl within the interval 0–3M) under conditions allowing adsorption of said protected oligonucleotide to said adsorbent.

The property of binding the protected oligonucleotide under conditions of high as well as low ionic strength means that the adsorbent in spite of its hydrophilic character also expresses a low but measurable non-ionic binding that most likely is hydrophobic in nature.

In subsequent steps, the adsorbed protected oligonucleotides are deprotected and the desired full length oligonucleotide eluted by the use of aqueous solvents, preferably water, containing the appropriate buffering components.

Appropriate conditions for the different steps should not cause any significant undesired degradation of the oligonucleotide to be purified.

Samples

The sample may be any sample containing the desired oligonucleotide with a hydrophobic protecting group. It may be the crude material coming from the synthesis of the oligonucleotide after release from the solid phase matrix. Thus the sample may, in addition to the desired oligonucleotide and reagents added for the release, also contain water-soluble forms of failure oligonucleotides (failure sequences) formed in non-wanted or incomplete reactions during the synthesis. The failure oligonucleotides may be in protected and/or unprotected form.

Steps

Adsorption of the protected oligonucleotide to the adsorbent.

The important matter is to provide conditions allowing the non-ionic binding between the protected oligonucleotide and the adsorbent. This means that at low ion concentration both the protected and unprotected oligonucleotides may be adsorbed in this step, although clear advantages are seen in arranging for a selective adsorption of protected oligonucleotides (i.e. a higher salt concentration). This in turn means that the conditions are not critical and crude samples may be applied directly more or less without any prepurification steps. After adsorption it is preferred to apply a washing step in order to remove non-adsorbed sample constituents including, if present, excess agents from cleavage of the oligonucleotide from the support used during the synthesis. In case both protected and unprotected oligonucleotides have been adsorbed it is advantageous to apply conditions permitting selective desorption of oligonucleotides not carrying the hydrophobic protecting group, i.e. to increase the salt concentration.

For the adsorption step and subsequent washing steps, the conditions are normally selected within the intervals:

Ionic strength: In principle the ionic strength may vary within wide ranges although washing steps utilizing a high ionic strength in the washing solutions are favourable for high purity of the end product. Normally ionic strengths corresponding to concentrations of NaCl within 0–4M, preferably 0.1–3M or 0.5–3M, are efficient. Suitable salts are NaCl or other inorganic water-soluble salts.

Temperature: Normally within 0°–50° C., with preference for 10°–40° C.

pH: alkaline, that usually means a pH-value within 7–14, with preference for 8–12.

Higher salt concentrations will elute non-protected oligonucleotides.

Deprotection. This preferably takes place while the protected oligonucleotide is in an adsorbed state. The conditions are the same as normally applied for each respective protecting group, although it is preferred to keep the conditions so that the formed deprotected oligonucleotides will remain adsorbed (via anion exchange). This normally means that in case the protecting group is transformed to a hydrophobic compound this latter also will remain adsorbed. Typically, the adsorbent is incubated with a cleavage solution matching the protecting group in order for the deprotection to take place. For hydrolytically releasable groups, for instance DMTr, the solution often contains a relatively strong organic carboxylic acid, such as trifluoroacetic acid, as the cleavage agent. Potentially also dichloro and trichloro acetic acid may be used. In order to secure that the deprotected oligonucleotides remains adsorbed the ionic strength is normally held as low as possible (often below 0.5M). Typically the temperature and incubation times are selected within the intervals 0°–40° C. and 1–60 minutes, respectively, bearing in mind that a lower temperature requires a longer incubation times.

Elution of deprotected oligonucleotides. This step is performed in the usual manner for the elution of oligonucleotides from hydrophilic anion exchangers. The solutions are aqueous, most preferably water, containing appropriate salts (usually inorganic water-soluble salts, such as NaCl) and buffering components. Most preferably the elution is carried out with a salt gradient in order to elute the oligonucleotides according to length. The start and end concentrations as well as the steepness of the gradient will depend on the amount and length of the oligomers to be separated. Elution may also be performed by stepwise changing the ionic strength. Normally the ionic strength is within in the interval 0–3M and the steepness within the interval 5–40 column volumes.

The hydrophobic compound derived from the protecting group, will after the elution of the oligonucleotides, remain on the adsorbent. The compound may be eluted therefrom by the use of aqueous solutions containing a hydrophobic water-soluble cosolvent, for instance a lower alcohol, such as isopropanol and ethanol.

As indicated, application of the appropriate order of adsorption, deprotection and elution will lead to high purification on the selected hydrophilic anion exchange adsorbent. In case one would select a protocol in which the adsorbed protected oligonucleotides are desorbed before deprotection, this will require extra ion exchange steps in order to separate the desired full length oligonucleotide from shorter forms.

The adsorbent

Suitable adsorbents are pronouncedly hydrophilic but with a weak but measurable ability to bind non-ionically to a modified oligonucleotide carrying one or more hydrophobic groups. The adsorbent shall show no or a very minor unspecific adsorption of proteins and peptides, such as cytochrome C, ovalbumin and angiotensin, but still has the capacity to bind DMTr-protected oligonucleotides at high ionic strength (for instance corresponding to a concentration of 0.5–3M NaCl). Structurally this means that the adsorbent should expose an excess hydrophilic groups, such as alcoholic OH-, anion exchange groups, oligo- and polyethylene oxide groups etc., on its surface in comparison to hydrophobic groups.

Examples of hydrophobic groups that may be present are hydrocarbyls comprising aromatic rings, and/or straight, branched or cyclic alkyl groups or chains.

Examples of anion-exchanging groups are amino groups, in particular tertiary groups such as diethylaminoethyl and quarternary amino groups, such as trialkylammoniumalkyl (e.g. trimethylammonium-, triethylammonium- and 2-hydroxyethyldiethylammoniumalkyl), dialkylarylammonium-alkyl (e.g. dimethylaniliniumalkyl) and ring-containing ammonium groups (e.g. N-methyl (piperidinium)- and pyridiniumalkyl). The alkyl group linking the nitrogen to the adsorbent may be a short alkylene chain, such as ethylene. The number of anion exchange groups of the adsorbent is not critical for the method. Anion exchangers having the appropriate degree of nonspecific adsorption and between 1–1,000 µmole, preferably 50–1,000 µmole, of anion exchanging groups per ml media may be used. People within the field will have no difficulties in finding the appropriate combinations of ion exchange capacity, sample volume and conditions for adsorption, deprotection and elution keeping in mind the general rules for the invention given above.

Several potential useful adsorbents can be imagined from the scientific and patent literature. For instance chromatography adsorbents made from water-insoluble polymers based on crosslinked dextran, polyacrylamide, poly (hydroxyalkyl methacrylate) and other polymethacrylates, cellulose etc. onto which appropriate anion exchange and hydrophobic groups have been attached. In some cases the base polymer as such may provide the sufficient hydrophobicity.

The adsorbent may also be built of a strongly hydrophobic base matrix, such as polydivinylbenzene and polystyrene (optionally as copolymers with each other), polyethylene, polypropylene etc., which matrix has been hydrophilised by being coated with any of the above-mentioned polymers or derivatized on their surface to exhibit the above-mentioned hydrophilicity and anion exchange groups. In this case the appropriate ability to bind non-ionically may originate from the base matrix as such or from the derivatization.

The adsorbent is normally porous and may be in particle forms (such as beads) or continuous (monolithic). The particle forms may be used in the form of packed or fluidised beds (expanded beds)

Best mode

At the priority date the most preferred adsorbent was commercially available under the name of SOURCE® 30Q (Pharmacia Biotech AB, Uppsala, Sweden). According to the manufacturer this media is a rigid, porous, spherical monodisperse anion exchanger. The base matrix is made of polystyrene/divinyl benzene beads that have been coated with a layer of crosslinked alkylethers containing hydroxyl groups. The anion exchange groups are of the quarternary type (trimethylammonium) and are attached to the coating via hydrophilic spacer arms. The ability to bind to protected oligonucleotides (in particular oligonucleotides having hydrophobic groups at their 5-terminal position) may derive from the basic polystyrene/divinyl benzene base matrix or from groups introduced during the hydrophilization (for instance alkyl ether groups).

According to the best mode of the invention, oligonucleotide analogues in which at least one oxygen in their phosphate group is replaced with sulphur are purified (phosphorothioate and phosphorodithioate oligomers).

The best mode of the invention is further illustrated in the experimental section.

EXPERIMENTAL SECTION

The Sample: 35 ml of a 25% ammonia solution containing 4460 optical density units (ODU's) measured at 260 nm, 1 cm path length. The processed oligonucleotide was a phosphorothioate 25-mer, synthesized on an OligoPilot(R) DNA/RNA Synthesiser. The amount of 25-mer corresponding to full length product was 2359 ODU's as estimated from absorbance measurements and capillary electrophoresis of the crude material.

The column and the adsorbent: The media SOURCE® 30Q (Pharmacia Biotech AB, Uppsala, Sweden) was packed into a HR16 column (Pharmacia Biotech AB) resulting in a packed bed of 16×110 mm. All chromatographic procedures were performed on BioPilot(R) (chromatography system, Pharmacia Biotech AB). The following steps were applied in the given order:

1. The sample was applied onto the column whereafter the column was washed with two column volumes (Cv) of 10 mm NaOH followed by two Cv of 3.0M NaCl, pH 12, and once again with 2×Cv of 10 mM NaOH. In this step the non-dimethoxytritylated failure sequences were washed away.

2. The column was washed with 0.4% trifluoroacetic acid until acidic pH in the eluate, approximately 3×Cv, and then left for 20 minutes to obtain complete cleavage of the DMTr group from the 25-mer. The column was then reequillibrated to basic pH with 10 mM NaOH.

3. The 25-mer was then eluted and further purified from shorter sequences by applying a linear NaCl gradient from 0.8–1.9M NaCl at constant pH 12 over 25×Cv. Fractions of 10 ml each were collected and analysed by capillary electrophoreses. The fractions in which the full length product constituted more than 92 % of the oligonucleotides were pooled.

4. The column was finally cleaned by applying 2×Cv of 2M NaCl in isopropanol (30% (w/w)).

Analysis of the pool revealed a yield of 66.37 mg of the product with a purity of 98% as determined by capillary electrophoreses. The overall recovery was 76%. The complete chromatographic process took less than three hours.

I claim:

1. A method for the purification of a synthetic oligonucleotide from failure sequences, comprising:

contacting a sample containing a desired protected oligonucleotide in protected water-soluble form with a hydrophilic adsorbent exhibiting anion exchange groups under conditions permitting binding of said protected oligonucleotide to said adsorbent, wherein said adsorbent binds the protected oligonucleotide under conditions of high as well as low ionic strength;

deprotecting the adsorbed protected oligonucleotide while adsorbed; and separating said adsorbed protected or deprotected oligonucleotide from failure sequences.

2. The method according to claim 1, wherein the adsorbent after adsorption of the desired nucleotide is incubated with a solution that a. comprises a deprotecting agent for cleaving off the protecting group and b. has an ionic strength maintaining the deprotected oligonucleotide adsorbed to the adsorbent; said incubation being performed under sufficient time for deprotection.

3. The method according to claim 2, wherein the desired oligonucleotide is desorbed from the adsorbent after deprotection.

4. The method according to claim 3, wherein the desorption of the desired oligonucleotide is carried out with a salt gradient.

5. The method of claim 1, wherein said failure sequences are separated from said protected oligonucleotide while said protected oligonucleotide is bound to said adsorbent.

* * * * *